United States Patent [19]
Shemano

[11] 3,937,835
[45] Feb. 10, 1976

[54] PHARMACEUTICALLY USEFUL SULFUR CONTAINING HETEROCYCLIC DERIVATIVES

[75] Inventor: Irving Shemano, Cincinnati, Ohio

[73] Assignee: Richardson-Merrell Inc., Wilton, Conn.

[22] Filed: June 15, 1973

[21] Appl. No.: 370,424

[52] U.S. Cl.................................. 424/275; 424/276
[51] Int. Cl.² ................... A61K 31/38; A61K 31/39
[58] Field of Search............................ 424/275, 276

*Primary Examiner*—Jerome D. Goldberg
*Attorney, Agent, or Firm*—L. Ruth Hattan; Eugene O. Retter; George W. Rauchfuss, Jr.

[57] ABSTRACT

Compounds of the following general formula are useful in the treatment of conditions of delayed hypersensitivity.

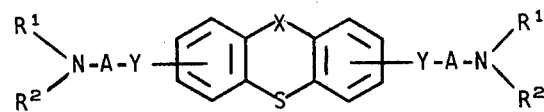

wherein X represents a bond, —$CH_2$—, or oxygen; Y represents a vinlyene group, —CH(OH)—, carbonyl, oxygen, divalent sulfur, or carbonyloxy with the proviso that when Y is oxygen, divalent sulfur or carbonyloxy, X represents a bond; A represents a straight or branched alkylene chain of from 1 to 6 carbon atoms with the proviso that when Y is vinlyene, A contains from 1 to 5 carbon atoms; and with the proviso that when Y is carbonyloxy, A contains from 2 to 6 carbon atoms; each of $R^1$ and $R^2$ is selected from hydrogen, a straight or branched lower alkyl group of from 1 to 4 carbon atoms; or alkenyl of 3 to 6 carbon atoms having the vinyl unsaturation in other than the 1-position, and pharmaceutically acceptable acid addition salts thereof.

9 Claims, No Drawings

PHARMACEUTICALLY USEFUL SULFUR CONTAINING HETEROCYCLIC DERIVATIVES

FIELD OF INVENTION

This invention relates to the use of bis-basic substituted sulfur containing heterocyclic derivatives.

DESCRIPTION OF THE PRIOR ART

Bis-basic ether and thioether derivatives of dibenzothiophene are described in U.S. Pat. 3,673,191. Bis-basic ketone derivatives of dibenzothiophene are described in Belgian Pat. 766,577. Bis-basic ketones of thioxanthene are described in Great Britain Pat. 1,312,534 which is equivalent to pending U.S. application Ser. No. 137,055. Bis-basic ketones of phenoxathiin are described in Netherlands 72/09010 which is equivalent ot pending U.S. application Ser. No. 158,122. Each of these references disclose the compounds therein as being useful as antiviral agents. These disclosures do not describe or suggest the use of the compounds in treating conditions of delayed hypersensitivity.

SUMMARY OF INVENTION

Bis-basic derivatives of the following formula are useful in treating conditions of delayed hypersensitivity.

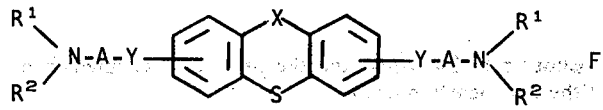 Formula I wherein X represents a bond, —CH$_2$—, or oxygen; Y represents a vinylene group, —CH(OH)—, carbonyl, oxygen, divalent sulfur, or carbnoyloxy with the proviso that when Y represents oxygen, divalent sulfur or carbonyloxy, X represents a bond; A represents a straight or branched alkylene chain of from 1 to 6 carbon atoms with the proviso that when Y is a vinylene group, A contains from 1 to 5 carbon atoms, and with the proviso that when Y is carbonyloxy, A contains from 2 to 6 carbon atoms; each of R$^1$ and R$^2$ represents hydrogen, a straight or branched lower alkyl group of from 1 to 4 carbon atoms, or alkenyl of 3 to 6 carbon atoms having the vinyl unsaturation in other than the 1-position; and pharmaceutically acceptable acid addition salts thereof.

DETAILED DESCRIPTION OF INVENTION

As can be seen from the above general Formula I the compounds of this invention may be dibenzothiophene derivatives when X is a bond, or thioxanthene derivatives when X is —CH$_2$—, or phenoxathiin derivatives when X is oxygen.

In the above general Formula I one of the basic substituent groups as represented by

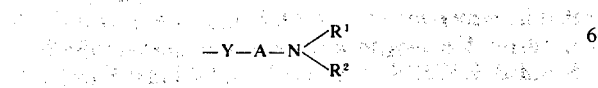

is attached at any carbon atom of one benzenoid ring of the tricyclic nucleus, and the other basic substituent is attached at any carbon atom of the other benzenoid ring.

Illustrative examples of straight or branched alkylene chains which A represents in general Formula I are methylene, ethylene, propylene, butylene, pentylene, hexylene, isobutylene, 2-methylethylene, and 3-ethylbutylene.

Illustrative examples of straight or branched lower alkyl groups which R$^1$ and R$^2$ may represent in general Formula I are methyl, ethyl, n-propyl, n-butyl, isobutyl, isopropyl, and tert-butyl.

Pharmaceutically acceptable acid addition salts of the base compounds of this invention are those of any suitable inorganic or organic acid. Illustrative suitable inorganic acids are hydrochloric, hydrobromic, sulfuric, and phosphoric acids. Illustrative suitable organic acids are lower aliphatic hydrocarbon monocarboxylic acids, such as, glycolic or lactic acid; lower aliphatic lower alkoxy-hydrocarbon monocarboxylic acids, such as, methoxyacetic or ethoxyacetic acids; lower aliphatic lower alkanoyl-hydrocarbon monocarboxylic acids, such as, pyruvic acid; lower aliphatic hydrocarbon dicarboxylic acids, such as malonic, succinic, methylsuccinic, glutaric, α-methylglutaric, β-methylglutaric, itaconic, maleic, citraconic, homocitraconic, or fumaric acid; lower aliphatic hydroxy hydrocarbon dicarboxylic acids, such as, malic or tartaric acid; lower aliphatic lower alkoxy-hydrocarbon dicarboxylic acids; such as, α,β-dimethoxysuccinic or ethoxymaleic acid; lower aliphatic hydrocarbon tricarboxylic acids, such as, aconitic or tricarballylic acid; lower aliphatic hydroxy-hydrocarbon tricarboxylic acids, such as, citric acid. Additionally organic sulfonic acids, such as lower alkane sulfonic acids, for example, methanesulfonic or ethanesulfonic acid, or lower hydroxy-alkane sulfonic acids, for example, 2-hydroxyethane sulfonic acid are suitable. Particularly useful are pharmacologically acceptable acid addition salts with mineral acids, such as, hydrochloric acid. Mono- or di-acid salts may be formed, and the salts may be hydrated, for example, monohydrate, or substantially anhydrous.

Illustrative examples of compounds of general Formula I are 2,8-bis(4-aminobutoxy)dibenzothiophene, 2,8-bis(2-diethylaminoethylthio)dibenzothiophene, 3,7-bis(2-isopropylaminoethoxy)dibenzothiophene, bis(3-diallylaminopropyl)dibenzothiophene-2,8-dicarboxylate, bis(3-diisopentylaminopropyl)dibenzothiophene-2,6-dicarboxylate, 2,8-bis(5-diethylaminovaleryl)dibenzothiophene, 2,8-bis(2-dibutylaminoacetyl)dibenzothiophene, 3,7-bis(3-dimethylaminopropionyl)dibenzothiophene, α,α'-bis(3-diethylaminopropyl)dibenzothiophene-2,6-dimethanol, 2,8-bis[4-(dimethylamino)-1-butenyl]dibenzothiophene, 2,7-bis(2-diethylaminoacetyl)thioxanthene, 1,6-bis(3-diallylaminopropionyl)thioxanthene, α,α'-bis(3-diethylaminopropyl)thioxanthene-2,7-dimethanol, α,α'-bis(3-dimethylaminoethyl)thioxanthene-1,6-dimethanol, 2,7-bis(4-diethylamino-1-butenyl)thioxanthene, 1,6-bis(3-dipropylamino-1-propenyl)thioxanthene, 2,8-bis(5-dimethylaminovaleryl)phenoxathiin, 2,7-bis(3-dibutylaminopropionyl)phenoxathiin, 3,7-bis(4-ethylaminobutyryl)phenoxathiin, α,α'-bis(2-diethylaminoethyl)phenoxathiin-2,7-dimethanol, and 2,8-bis(5-dimethylamino-1-pentenyl)phenoxathiin.

The compounds of general Formula I may be prepared by several methods. The compounds of general Formula I wherein X is a bond, and Y is oxygen or divalent sulfur, that is, bis-basic ether or thioether derivatives of dibenzothiophene may be prepared by the reaction of one equivalent of a dibenzothiophene diol or dithiol derivative with two equivalents of a haloalkylamine of the formula

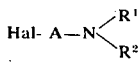   Formula II wherein Hal represents chlorine, bromine or iodine; A is a straight or branched alkylene chain of from 1 to 6 carbon atoms; and each of $R^1$ and $R^2$ is hydrogen, a straight or branched lower alkyl group of from 1 to 4 carbon atoms; or alkenyl of 3 to 6 carbon atoms having the vinyl unsaturation in other than the 1-position; in the presence of a base. Typical haloalkylamines are, for example, N,N-diethyl-2-chloroethylamine or N,N-diisopropyl-3-chloropropylamine.

Alternatively the bis-basic ether or thioether derivatives of dibenzothiophene may be prepared by the reaction of a bis-ω-haloalkylether or thioether derivative of the formula

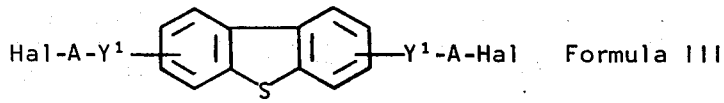   Formula III wherein $Y^1$ is oxygen or divalent sulfur, and A and Hal have the meanings defined above, with an amine of the formula

   Formula IV wherein $R^1$ and $R^2$ have the meanings defined hereinbefore. The bis-ω-haloalkylether or thioether of Formula III is obtained by the reaction of a dibenzothiophene-diol or dithiol with a haloalkylhalo derivative, that is, Hal-A-Hal wherein A is a straight or branched alkylene chain of from 1 to 6 carbon atoms, and Hal is chlorine, bromine or iodine in the presence of a base.

Suitable bases for the above described reactions are sodium methoxide, sodium hydride, sodium amide, sodium hydroxide, and potassium hydroxide. Suitable solvents include aromatic hydrocarbons, such as benzene, toluene and xylene; halogenated aromatics, such as, chlorobenzene; aprotic solvents, such as, N,N-dimethylformamide, N,N-dimethylacetamide, and dimethylsulfoxide; alcohols, such as, ethanol or isopropyl alcohol; ketones, such as, acetone; ethers, such as, tetrahydrofuran or dioxane; water; or mixtures of these solvents.

When either sodium methoxide, sodium amide or sodium hydride, for example, is used as the base, the reaction is carried out in an anhydrous medium, such as anhydrous toluene or chlorobenzene. About 2.5 equivalents of the base is added to a suspension of a dibenzothiophene-diol or dithiol, in the anhydrous solvent, and the mixture is heated. In the case where sodium methoxide is used, the methanol formed may be removed advantageously by azeotropic distillation. About 2.5 equivalents of the halide, either a haloalkylamine or a haloalkylhalo derivative is added and the mixture heated to reflux for a period which may vary from about 4 to 24 hours. The products are isolated by customary procedures.

In the method where an alkali hydroxide, such as potassium hydroxide is used as the base, two different procedures may be used. In the one procedure a 25 to 50 percent aqueous solution of the alkali hydroxide (about 2.5 equivalents) is added to a suspension of a dibenzothiophene-diol or dithiol in a suitable aromatic solvent, for example, xylene. This mixture is then heated to boiling, stirring being optional, and the water removed by azeotropic distillation. The reaction mixture, now being essentially anhydrous, is treated with about 2.5 equivalents of either a haloalkylamine or a haloalkylhalo derivative. In the other procedure the reaction is carried out in a heterogenous medium of water and an aromatic hydrocarbon, such as, toluene or xylene. For example, one equivalent of a dibenzothiophene-diol or dithiol is suspended in the aromatic hydrocarbon. To this suspension is added about 2.5 equivalents of a hydrohalide salt of a haloalkylamine derivative or a haloalkylhalo derivative in a minimum volume of water after which a 25 to 50% solution of the alkali hydroxide (about 5 equivalents when using a haloalkylamine derivative and about 2 equivalents when using a haloalkylhalo derivative) is added with efficient stirring. This mixture is heated to reflux for about 6 to 24 hours, and the product is isolated from the hydrocarbon layer.

The reaction between the bis-ω-haloalkylether or thioether derivative of Formula III and an amine as represented by Formula IV may be carried out under a variety of conditions. For example, the compound of Formula III may be heated together with a large excess of the amine, the excess amine serving as both the reaction medium and the hydrohalide acceptor. Or, 1 equivalent of the bis(ω-haloalkyl)ether or thioether, and 4 equivalents of the amine may be heated together in one of a number of different types of solvents, for example, in aromatic solvents, such as, benzene, toluene, xylene, or chlorobenzene; or lower molecular weight alcohols, such as, methanol, ethanol or isopropyl alcohol; or lower molecular weight ketones, such as, acetone or methyl ethyl ketone. The reaction between the halo compound and the amine is usually promoted by the addition of either sodium or potassium iodide, the iodide being used in either catalytic or stoichiometric amounts. In some cases, it may be advantageous to use only 2 equivalents of the amine for each equivalent of the bis-ω-haloalkylether or thioether, an excess of either powdered potassium carbonate or sodium carbonate being used as the hydrohalide acceptor.

Additional methods for the preparation of bis-basic ether and thioether derivatives of dibenzothiophene, that is, compounds of general Formula I wherein X is a bond and Y is oxygen or divalent sulfur, are set forth in U.S. Pat. 3,673,191 columns 7, 8, and 9 and the appropriate portion thereof are incorporated herein by reference thereto.

The compounds of general Formula I wherein X is a bond and Y is carbonyloxy, that is, bis-basic ester derivatives of dibenzothiophene may be prepared by several methods. For example, a dibenzothiophene dicarboxylic acid or a reactive derivative thereof, such as, an acid halide or ester of the formula

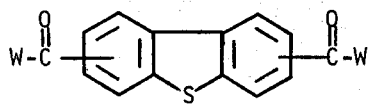   Formula V wherein W is OH, halogen, such as chlorine or bromine, or lower alkoxy, such as, methoxy or ethoxy, is reacted with an aminoalkanol of the formula

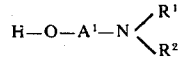   Formula VI wherein $A^1$ is a straight or branched alkylene chain of from 2 to 6 carbon atoms, and each of $R^1$ and $R^2$ is hydrogen, a straight or branched lower alkyl group of from 1 to 4 carbon atoms, or alkenyl of 3 to 6 carbon atoms having the vinyl unsaturation in other than the 1-position. The esterification can be achieved by allowing the dibenzothiophene dicarboxylic acid, where W in the above Formula V is hydroxy, to react with an appropriate aminoalkanol in an inert solvent in the presence of a catalyst and employing general methods for removing water from the reaction site. Preferred solvents are chloroform, isopropyl alcohol, dioxane, and toluene. The reaction may be catalyzed by the use of mineral acids including hydrochloric, sulfuric or certain organic acids such as p-toluene-sulfonic acid. Methods whereby water can be removed from the reaction include the use of water scavengers such as the carbodiimides or by the azeotropic removal of water. The reaction will proceed at temperatures ranging from 50°–150°C over a period of 6 to 72 hours depending upon the solvent and catalyst.

Preferably, the esterification can be achieved by allowing the acid halide, where W in the above Formula V is halogen, to react with the appropriate aminoalkanol. The esters of this invention can be produced in a variety of inert solvents over a wide range of temperatures and reaction time. The solvents of choice include chloroform, dioxane, tetrahydrofuran, and the aromatic solvents such as benzene and toluene. In chloroform, the reaction is generally complete within one hour at the reflux temperature of the solvent, although the reaction time can range from 15 minutes to 3 days.

The bis-basic ester derivatives of dibenzothiophene may also be prepared by a transesterification reaction in which a (lower)alkoxy ester of the dibenzothiophene dicarboxylic acid, where W in the above Formula V is, for example, methoxy or ethoxy, is reacted with the appropriate aminoalkanol under suitable conditions. This type of reaction is catalyzed by alkaline or acid catalysts and is reversible. The basic esters may be obtained by causing the equilibrium to be shifted by removing the lower alkanol component or by employing a large excess of the aminoalkanol. Preferably, the reaction is carried out by removing the lower alkanol component with the use of an alkaline catalyst. The lower alkanol may be removed by direct distillation or distillation with a suitable solvent. Suitable alkaline catalysts are alkali metals, such as, sodium or potassium; alkali lower alkoxides, such as, sodium methoxide or sodium ethoxide; or alkali amides such as lithium or sodium amide. Suitable solvents are those forming an azeotropic distillation mixture with the lower alkanol, for example, benzene or toluene, or a solvent which boils sufficiently higher than the alkanol to permit removal of the alkanol by distillation at a temperature below that of the boiling range of the solvent.

The compounds of general Formula I wherein Y is carbonyl may be prepared by an amination reaction of a bis-ω-haloalkanoyl derivative of the formula

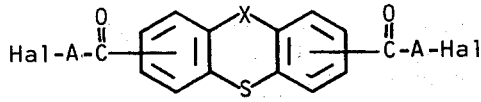

Formula VII wherein Hal is chlorine, bromine or iodine; A is a straight or branched alkylene chain of from 1 to 6 carbon atoms; and X is a bond, —$CH_2$— or oxygen; with an amine of the formula $HNR^1R^2$ wherein each of $R^1$ and $R^2$ is hydrogen, a straight or branched lower alkyl group of from 1 to 4 carbon atoms, or alkenyl of 3 to 6 carbon atoms having the vinyl unsaturation in other than the 1-position.

The amination reaction may be carried out under a variety of conditions. For example, a compound of Formula VII may be heated together with a large excess of the amine, the excess amine serving as the reaction medium and the hydrohalide acceptor. This method is particularly suitable for readily available amines, the excess of which can be easily removed from the reaction mixture by, for example, distillation at reduced pressure or by washing the product with water. Or, one equivalent of a compound of Formula VII and four equivalents of the amine, may be heated together in one of a number of different types of solvents, for example, in aromatic solvents, such as, benzene, toluene, or xylene; ethers, such as, tetrahydrofuran, or dioxane; ketones, such as, acetone or butanone; aprotic solvents, such as, N,N-dimethylformamide, N,N-dimethylacetamide, or dimethyl sulfoxide; or mixtures of these solvents with water. The reaction between a compound of Formula VII wherein Hal is Cl and the amine, is frequently promoted by the addition of either sodium iodide or potassium iodide, the iodide being used in either catalytic or stoichiometric amounts. In some cases, it may be advantageous to use only two equivalents of the amine for each equivalnet of the bis-ω-haloalkanoyl derivative, an excess of an inorganic base, such as, powdered sodium carbonate or potassium carbonate being used as the hydrohalide acceptor. The reaction will proceed normally in 12 hours to two weeks at temperatures of from −30° to 150°C.

Alternately, the amination reaction may be carried out on a derivative of a compound of Formula VII, such as, the bis-ketal derivative that may be prepared by allowing the bis-ω-haloalkanoyl derivative and an excess of ethyl orthoformate to react in the presence of an acid catalyst such as hydrochloric acid for several days in a polar solvent such as ethanol or tetrahydrofuran.

The bis-(ω-haloalkanoyl)dibenzothiophene derivatives, that is, compounds of Formula VII wherein X is a bond, wherein the position of substitution is 2,6- or 2,8- can be prepared by a Friedel-Crafts acylation of dibenzothiophene. Suitable acylating agents which may be used include chloroacetyl chloride, bromoacetyl bromide, 3-chloropropionyl chloride, 4-chlorobutyryl chloride, 5-chlorovaleryl chloride, 5-chloro-4-methylvaleryl chloride, and 5-chloro-3-methylvaleryl chloride.

The acylation reaction may be carried out in a variety of solvents and under catalysis of a variety of Lewis acids. The temperature and duration of the reaction may be varied to allow for optimum reaction conditions. A preferred procedure is to combine one equivalent of dibenzothiophene with 2.5 equivalents of an acylating agent in methylene chloride followed by portionwise addition of aluminum chloride. The temperature of the reaction is maintained below zero degrees with continuous stirring. After the additions are complete the temperature may be elevated to 25°–40°C for 12 to 36 hours. The reaction mixture is worked up in the usual manner by decomposing the complex with ice water/HCl. The product obtained is recrystallized from methylene chloride, chloroform, or the like. The procedure may be varied such that there is a reverse addition of acylating agent and Lewis acid, or a reverse addition of aromatic hydrocarbon and Lewis acid. The more reactive halogen derivative that is, the bis-(ω-iodoalkanoyl)dibenzothiophene, may be prepared from the corresponding bis-chloro derivative using a halogen exchange reaction under the conditions generally employed in the Conant-Finkelstein reaction.

The major product in the Friedel-Crafts acylation reaction is 2,8-bis-(ω-haloalkanoyl)dibenzothiophene. However, the course of the reaction is such that the major isomer is generally accompanied by significant quantities of other isomeric forms of bis-(ω-haloalkanoyl)dibenzothiophene. By the proper choice of crystallizing solvents these isomers can be separated.

The bis-(ω-haloalkanoyl)thioxanthene derivatives, that is, compounds of Formula VII wherein X is —CH$_2$—, wherein the position of substitution is 2,7-, and the bis-(ω-haloalkanoyl)phenoxathiin derivatives, that is, compounds of Formula VII wherein X is oxygen, wherein the position of substitution is 2,7- or 2,8- can be prepared by the same procedure as that described hereinabove for the preparation of the bis-(ω-haloalkanoyl)dibenzothiophene derivatives, by substituting respectively thioxanthene and phenoxathiin for dibenzothiophene in the procedure as described.

Suitable amines for use in the amination reaction include ammonia, or a compound which is a potential source of ammonia, for example, hexamethylenetetramine; primary amines, such as, ethylamine, propylamine and methylamine; and secondary amines, such as, diethylamine, dibutylamine diisopropylamine and dipentylamine.

The bis-basic ketone derivatives of Formula I wherein X is a bond, A is an alkylene chain of 3 to 6 carbon atoms, and R$^1$ and R$^2$ are other than hydrogen, may also be prepared by the reaction of a dinitrile derivative of dibenzothiophene with a Grignard reagent of the formula R$^5$Mg(CH$_2$)$_m$NR$^3$R$^4$ (Formula VIII) wherein R$^5$ is bromine or chlorine, $m$ is an integer of 3 to 6, and each of R$^3$ and R$^4$ is a straight or branched lower alkyl group of from 1 to 4 carbon atoms or alkenyl of 3 to 6 carbon atoms having the vinyl unsaturation in other than the 1-position. The reaction will proceed in from 1 to 24 hours at a temperature ranging from room temperature to about 80°C. The Grignard reagent, may be prepared by reacting magnesium and an aminoalkyl halide of the formula R$^5$(CH$_2$)$_m$NR$^3$R$^4$ wherein R$^5$, $m$, and —NR$^3$R$^4$ have the meaning defined hereinabove. A preferred solvent for this reaction is tetrahydrofuran. The dinitrile derivative of dibenzothiophene may be prepared from known diamines by aa Sandmeyer reaction on the tetrazonium salts or from known dibenzothiophene dicarboxylic acids by dehydration of the corresponding amides by standard procedures.

The bis-ketone derivatives of Formula I wherein X is —CH$_2$— or oxygen, A is an alkylene chain of from 3 to 6 carbon atoms and R$^1$ and R$^2$ are other than hydrogen, may also be prepared by the reaction of a Grignard reagent of the above Formula VIII with a bis-amide derivative of thioxanthene or phenoxathiin of the formula

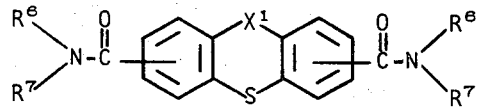

Formula IX wherein X$^1$ is —CH$_2$— or oxygen, and R$^6$ and R$^7$ are hydrogen or a lower alkyl group. The addition of the Grignard reagent, is carried out at low temperatures ranging from −70°C to 0°C, and the reaction mixture is then warmed at 0° to 80°C for 1 to 24 hours. The bis-amide derivatives may be prepared by generally known methods from the corresponding bis-acids.

The bis-basic ketone compounds of general Formula I wherein A is —CH$_2$CH$_2$—, and both of R$^1$ and R$^2$ are not hydrogen may also be prepared by a Mannich reaction of a bis-acetyl derivative of the formula

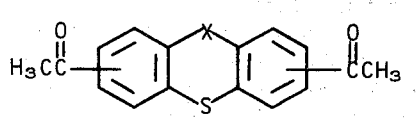 Formula X wherein X is a bond, —CH$_2$— or oxygen, with an amine of the formula HNR$^1$R$^2$ wherein R$^1$ and R$^2$ have the meanings defined in general Formula I except that both of R$^1$ and R$^2$ are not hydrogen, in the presence of formaldehyde. By combining one equivalent of a compound of Formula X and two or more equivalents the amine with three or more equivalents of formaldehyde the reaction will proceed in from a few minutes to 24 hours in solvents such as water, acetic acid, ethanol, butanol, dioxane, and tetrahydrofuran and at temperatures equivalent to the reflux temperature of the solvent. In this reaction either of two sources of formaldehyde may be employed. When formalin is used the reaction may be conducted with a suspension of a compound of Formula X or a co-solvent such as methanol may be added to allow the reaction to proceed in a homogeneous medium. When the source of formaldehyde is paraformaldehyde the reaction is carried out in an organic solvent such as those mentioned above. It is sometimes desirable to add a slight excess of hydrochloric acid to promote depolymerization of paraformaldehyde either during the reaction or at the end of the reaction.

The amine employed in this reaction may be added to the reaction medium as the hydrochloride salt or as the base form with subsequent in situ formation of the hydrochloride salt by the addition of hydrochloric acid. Typical amines which may be utilized in the above reaction include dimethylamine, dibutylamine, n-propylamine, diisopropylamine and methylamine.

The bis-acetyl derivative of Formula X may be prepared by a Friedel-Crafts acylation reaction on dibenzothiophene, thioxanthene or phenoxathiin or by a reaction of a dibenzothiophene, thioxanthene or phenoxanthiin bis-acid chloride with dimethyl-cadmium, which can be prepared from methyl Grignard and cadmium chloride. The bis-acid chlorides may be prepared from the corresponding bis-acids by conventional procedures.

The compound of general Formula I wherein Y is

are obtained by the reduction of the corresponding ketone derivatives, that is, compounds of Formula I wherein Y is carbonyl, the preparation of which is described hereinabove, using sodium borohydride as the reducing agent. Suitable solvents for this reaction are ethers, such as, tetrahydrofuran or dioxane, lower alcohols, such as, methanol or isopropyl alcohol, or water. The reaction time may vary from about 30 minutes to 25 hours, and the reaction temperature may vary from about −20° to 100°C. When water or methanol are used as solvents, a base such as sodium hydroxide is used in order to minimize the rate at which the sodium borohydride decomposes.

The compounds of general Formula I wherein Y is a vinylene group are prepared by dehydration of a compound of Formula I wherein Y is

and A contains 2 or more carbon atoms, the preparation of which is described above. Dehydration is accomplished by dissolving the bis-alkanol derivative in a high boiling solvent such as ethylene glycol or ethylene glycol monoethylether, adding a dehydrating agent, such as, concentrated HCl or concentrated $H_2SO_4$, then heating the reaction mixture to about 100°C on a steam bath for from one to thirty minutes. The vinylene derivatives may be isolated and purified by standard procedures. For example, the reaction mixture can be made alkaline and the product extracted with ether; or, any unreacted starting material may be separated from the final product by passage through a chromatographic column.

Introduction of an antigen, or a foreign substance, into an organism results in a specific immunological response changing the reactivity of the organism towards the antigen and substances closely resembling the antigen. This response is usually a heightened reactivity to antigen. This heightened reactivity is due in part to the production of antibodies which can result in an immediate hypersensitivity and in part to a cell-mediated immunity which can result in delayed hypersensitivity. Cell-mediated immunity is dependent upon the presence of cells sensitized to antigen, primarily thymus-modified lymphocytes, which specifically interact with the antigen. Macrophages are also involved in the processing of antigen and in the effector mechanisms leading to delayed hypersensitivity.

The type of substances which elicit delayed hypersensitivity are many and various. They may be organic chemicals, including drugs, simple chemical derivatives, or protein-containing antigens of micro-organisms, such as, bacteria, viruses, fungi or protozoa, or tissue antigens. Conditions of delayed hypersensitivity are associated with numerous pathological disorders, for example, contact hypersensitivity in the skin, rejection of tissue grafts or transplants, auto immune diseases and certain infectious diseases. Such pathological disorders often involve, in addition to the cell-mediated delayed hypersensitivity responses, humoral antibody responses involving the production of antigen-specific antibodies. Generally, treatment of these disorders has been with immunosuppressive agents, such as, purine analogs, folic acid antagonists, alkylating agents and corticosteroids. Such agents have been found to be non-specific in their immunosuppressant effects, that is, they suppress both the humoral antibody and delayed (cell-mediated) hypersensitivity responses. [Drug Therapy 1, no. 4, pp. 3–16 (1971)]. The compounds disclosed herein are unique in that they suppress only the delayed hypersensitivity response without concurrent suppression of the humoral immune response.

The compounds disclosed herein suppress delayed hypersensitivity responses thereby rendering the compounds useful in patients in the treatment of conditions of delayed hypersensitivity resulting from infectious diseases, specifically tuberculosis, streptococcus, staphylococcus and pneumococcus diseases, typhoid fever, undulant fever, chancroid, whooping-cough and leprosy; toxoids and vaccines, particularly diphtheria toxoid and smallpox vaccination; contact hypersensitivity in the skin, specifically from nickel salts, primrose or poison ivy, poison oak and paraphenylene diamine; tissue grafts and transplants; and auto immune diseases, specifically rheumatoid arthritis, systemic lupus erythematosus, glomerular nephritis, rheumatic fever, ulcerative colitis, diabetes mellitus, pernicious anemia, coeliac disease, primary atypical pneumonia, Hashimoto's thyroiditis, multiple sclerosis, peripherial neuritis, pemphigus, Addison's disease and Grave's disease.

The utility of the compounds disclosed herein in the treatment of conditions of delayed hypersensitivity is manifested by the ability of the compounds to suppress delayed hypersensitivity reactions in vitro in the macrophage migration inhibition test (MMIT) and in vivo in the experimental allergic encephalomyelitis (EAE) test, which are well recognized tests for detecting agents or compounds effective in treating conditions of delayed hypersensitivity. *Immunology for Students of Medicine*, 3rd edition, 1970, F. A. Davis Company, pp. 498–500; Federation Proceedings 27, No. 1, pp. 3–15, (1968); Advances in Immunology 5, pp. 131–208 (1966).

As used herein, the term patient means warm blooded animals, particularly mammals and humans. The compounds disclosed herein may be administered to a patient orally, parenterally or topically either alone or in the form of pharmaceutical preparations. Pharmaceutical preparations containing conventional pharmaceutical carriers and as active ingredients compounds of this invention can be employed in unit dosage forms such as solids, for example, tablets, capsules and pills, or liquid solutions, suspensions, or emulsions for oral and parenteral administration. The quantity of compound administered can vary over a wide range to provide from about 0.1 mg/kg (milligrams per kilogram) to about 200mg/kg of body weight of the patient per day, and preferably from about 1 mg/kg to 100mg/kg of body weight of the patient per day, to achieve the desired effect. Unit doses can contain from about 5 mg to 1.0 g of a compound of this invention and may be administered, for example, from 1 to 4 times daily.

The following specific examples are illustrative of the compounds of general Formula I.

EXAMPLE 1

2,8-Bis(2-dimethylaminoethoxy)dibenzothiophene dihydrochloride

To 200 ml of chlorobenzene is added 16.1 g (0.0745 mole) of 2,8-dihydroxydibenzothiophene, 16.8 g (0.156 mole) of 2-dimethylaminoethyl chloride and 8.3 g (0.154 mole) of sodium methoxide. The mixture is stirred and heated to reflux for 16 hours. The cooled reaction mixture is filtered and the filtrate is washed with several portions of water, then dried over anhydrous magnesium sulfate. The chlorobenzene solution is evaporated in vacuo. The oily residue is dissolved in ether and treated with ethereal hydrogen chloride to give 2,8-bis(2-dimethylaminoethoxy)dibenzothiophene dihydrochloride which is crystallized from methanol-butanone, M.P. 248°–250°C.

EXAMPLE 2

2,8-Bis(2-dimethylaminoethylthio)dibenzothiophene dihydrochloride

When the appropriate molar equivalent amounts of dibenzothiophene-2,8-dithiol is substituted for 2,8-dihydroxydibenzothiophene in the procedure described in Example 1, 2,8-bis(2-dimethylaminoethylthio)dibenzothiophene dihydrochloride is obtained.

Additional examples of the preparation of bis-basic ether and thioether derivatives of dibenzothiophene of Formula I are described in U.S. Pat. 3,673,191 at columns 9 to 12 and the appropriate examples disclosed therein are incorporated herein by reference thereto.

EXAMPLE 3

Bis(3-diethylaminopropyl)dibenzothiophene-2,8-dicarboxylate dihydrochloride

A solution of 7.6 g (0.025 mole) of dibenzothiophene-2,8-dicarbonyl chloride and 6.5 g (0.05 mole) of 3-diethylaminopropanol in 1 liter of chlorofrom is heated at reflux for two hours. The solution is concentrated to 500 ml, diluted with petroleum ether (75°–90°) and the precipitated solid is crystallized from methanol-isopropanol and finally from water-acetone to yield bis(3-diethylaminopropyl)dibenzothiophene-2,8-dicarboxylate dihydrochloride, M.P. 243°–245°C.

EXAMPLE 4

Bis(3-dibutylaminopropyl)dibenzothiophene-2,6-(and 2,8)-dicarboxylate dihydrochloride hemihydrate A solution of 12.0 g (0.038 mole) of a mixture of dibenzothiophene-2,6(and 2,8)-dicarbonyl chloride and 14.5 g (0.078 mole) of 3-dibutylaminopropanol in 500 ml of chloroform is heated at reflux for 24 hours. The solid which separates is treated with 25% aqueous sodium carbonate and the free base which results is extracted with ether, dried over anhydrous magnesium sulfate and treated with ethereal hydrogen chloride. The dihydrochloride salt is recrystallized several times from butanone to yield bis(3-dibutylaminopropyl)dibenzothiophene-2,6-(and 2,8)-dicarboxylate dihydrochloride hemihydrate consisting of C. 40% of the 2,6-isomer and 60% of the 2,8-isomer, M.P. 144°–146°c.

EXAMPLE 5

Bis(3-diisopentylaminopropyl)dibenzothiophene-2,6-(and 2,8)-dicarboxylate dihydrochloride When 3-diisopentylaminopropanol is used in place of 3-dibutylaminopropanol and the procedure of Example 4 is followed, bis(3-diisopentylaminopropyl)dibenzothiophene-2,6(and 2,8)dicarboxylate dihydrochloride is obtained after an additional crystallization from ethanol-butanone-pentane consisting of approximately 70% of the 2,6-isomer and 30% of the 2,8-isomer, M.P. 110°–118°C.

EXAMPLE 6

Bis(5-dimethylamino-2,2-dimethylpentyl)dibenzothiophene-2,6(and 2,8)-dicarboxylate dihydrochloride When 5-dimethylamino-2,2-dimethylpentanol is used in place of 3-dibutylaminopropanol and the procedure of Example 4 is followed, and after a final crystallization from methanol-butanone, bis(5-dimethylamino-2,2-dimethylpentyl)dibenzothiophene-2,6(and 2,8)-dicarboxylate dihydrochloride is obtained consisting of approximately 88% of the 2,6-isomer and 12% of the 2,8-isomer, M.P. 245°–251°C.

EXAMPLE 7

Bis(2-diethylaminoethyl)dibenzothiophene-2,6(and 2,8)-dicarboxylate dyhydrochloride When 2-diethylaminoethanol is used in place of 3-dibutylaminopropanol and the procedure of Example 4 is followed, bis(2-diethylaminoethyl)dibenzothiophene-2,6(and 2,8)-dicarboxylate dihydrochloride is obtained consisting of approximately 74% of the 2,6-isomer and 26% of the 2,8-isomer, M.P. 219°–225°C.

EXAMPLE 8

Dibenzothiophene-2,6(and 2,8)-dicarboxylic acid

To 800 ml of carbon disulfide cooled to −10°C is added 56 g (0.42 mole) of aluminum chloride and 36.8 g (0.2 mole) of dibenzothiophene. To this mixture is added, with stirring, 101 g (0.8 mole) of oxalyl chloride dissolved in 100 ml of carbon disulfide and the resulting brown mixture is stirred at −10°C for 4 hours and at 28°C for 64 hours. The mixture is decomposed with cold dilute hydrochloric acid, and after removal of carbon disulfide, the product is filtered and purified by extraction with dilute sodium hydroxide. The alkaline solution is filtered and converted back to acid. The product does not melt below 320°C.

EXAMPLE 9

Dibenzothiophene-2,6(and 2,8)-dicarbonyl chloride

Dibenzothiophene-2,6(and 2,8)dicarbonyl chloride is prepared from dibenzothiophene-2,6(and 2,8)dicarboxylic acid by the thionyl chloride-pyridine method and purified by crystallization from toluene, M.P 235°–237°C.

EXAMPLE 10

2,8-Bis(bromoacetyl)dibenzothiophene

To a solution of 5.0 g (0.019 mole) of 2,8-diacetyldibenzothiophene in 200 ml of chloroform is added dropwise 6.1 g (0.038 mole) of bromine in 25 ml of chloroform with stirring under gentle reflux. After refluxing for an additional hour the reaction mixture is cooled and the precipitate filtered and crystallized from acetic acid to give 2,8-bis(bromoacetyl)dibenzothiophene, M.P. 187°–189°C. (dec.).

EXAMPLE 11

2,6-Bis(bromoacetyl)dibenzothiophene

Following the procedure of Example 10, only substituting for 2,8-diacetyldibenzothiophene, 5.0 g (0.019 mole) of 2,6-diacetyldibenzothiophene, 2,6-bis(bromoacetyl)dibenzothiophene is obtained.

EXAMPLE 12

2,8-Bis(dimethylaminoacetyl)dibenzothiophene dihydrochloride

A mixture of 18.4 g (0.05 mole) of 2,8-bis(bromoacetyl)dibenzothiophene and 25 g (0.57 mole) of dimethylamine in 350 ml of tetrahydrofuran is heated at 60°C for 3 hours in a stainless steel reaction bomb. The excess amine and solvent are removed in vacuo, and the resulting residue is dissolved in ether and treated with ethereal HCl to give 2,8-bis(dimethylaminoacetyl)dibenzothiophene dihydrochloride which is recrystallized from methanol-ether. M.P. >340°C

EXAMPLE 13

2,6-Bis(dimethylaminoacetyl)dibenzothiophene dihydrochloride

Following the procedure of Example 12, only substituting for 2,8-bis(bromoacetyl)dibenzothiophene, 18.4 g (0.05 mole) of 2,6-bis(bromoacetyl)dibenzothiophene, 2,6-bis(dimethylaminoacetyl)dibenzothiophene dihydrochloride is obtained.

The preparation of additional examples of bis-basic ketone derivatives of dibenzothiophene of general Formula I and appropriate starting materials are set forth in Belgian patent 766,557 of which the appropriate examples are incorporated herein by reference thereto.

EXAMPLE 14

2,8-Bis(4-diethylaminobutyryl)thioxanthene dihydrochloride

A mixture of 32.6 g (0.08 mole) of 2,8-bis(4-chlorobutyryl)thioxanthene, 2 g of potassium iodide, 100 ml of diethylamine and 100 ml of tetrahydrofuran is heated for 24 hours with stirring in a Paar bomb at 110°C. Upon cooling, the mixture is evaporated to near dryness. The residue is dissolved in methylene chloride, washed with water then with saturated NaCl solution, dried over magnesium sulfate and filtered. The filtrate is evaporated to near dryness and recrystallized several times from methanol-diethyl ether and from acetone-methanol to give 2,8-bis(4-diethylaminobutyryl)thioxanthene dihydrochloride. M.P. 188°–191°C.

EXAMPLE 15

2,8-Bis(2-diethylaminoacetyl)thioxanthene dihydrochloride hydrate

A mixture of 35.1 g (0.10 mole) of 2,8-bis(2-chloroacetyl)thioxanthene, 2 g of potassium iodide, 200 ml of diethylamine and 500 ml of tetrahydrofuran is warmed on a steam bath and allowed to stand at room temperature for 7 days with occasional shaking then filtered. The filtrate is evaporated to dryness leaving a residue which is dissolved in dilute HCl and filtered. The filtrate is made alkaline, extracted with methylene chloride, washed with water then saturated NaCl solution, dried over magnesium sulfate and filtered. The filtrate is acidified with ethereal HCl, and the resulting product is recyrstallized from diethyl ether and methanol. After drying in vacuo and hydrating in a constant humidity chamber, 2,8-bis(2-diethylaminoacetyl)thioxanthene dihydrochloride hydrate is obtained. M.P. 122°–124°C.

EXAMPLE 16

2,7-Bis(2-chloroacetyl)thioxanthene

To a mixture of 99.18 g (0.5 mole) of thioxanthene, 141.0 g (1.45 mole) of 2-chloroacetyl chloride and 3 liters of dried methylene chloride, cooled to −20°C, is added slowly over 1/2 hour 146.7 g (1.1 mole) of aluminum chloride maintaining a temperature below −10°C. The reaction mixture is allowed to warm slowly to room temperature then refluxed for 4 hours. Upon cooling to room temperature, the mixture is decomposed by pouring into 2 liters of ice water and the layers are separated. The aqueous layer is extracted with methylene chloride after which the methylene chloride layers are combined and evaporated to a small volume and cooled. The resulting solid is filtered off and recrystallized from acetone to give 2,7-bis(2-chloroacetyl)thioxanthene. M.P. 175°–177°C.

EXAMPLE 17

2,7-Bis(4-chlorobutyryl)thioxanthene

Following the procedure of Example 16, only substituting for 2-chloroacetyl chloride, 173.3 g (125 mole) of 4-chlorobutyryl chloride the solid obtained is recrystallized from pentane and from heptane-benzene to give 2,7-bis(4-chlorobutyryl)thioxanthene. M.P. 115°–116°C.

The preparation of additional examples of bis-basic ketone derivatives of thioxanthene of general Formula I and appropriate starting materials are disclosed in Great Britain patent 1,312,534 which is equivalent to pending U.S. application Ser. No. 137,055, and of which the appropriate examples are incorporated herein by reference thereto.

EXAMPLE 18

2,7-Bis(5-chloroacetyl)phenoxathiin

2,8-Bis(5-chloroacetyl)phenoxathiin

To a mixture of 100.0 g (0.5 mole) phenoxathiin, 141.1 g (1.25 mole) of 2-chloroacetyl chloride and 3 liters of dried methylene chloride cooled to −20°C is added slowly over one-fourth hour 146.7 g (1.1 moles) of aluminum chloride, maintaining a temperature of below −10°C. The reaction mixture is allowed to warm slowly to room temperature and then refluxed for 4 hours and cooled to room temperature. The mixture is decomposed by pouring cautiously into 3 liters of ice water, and the layers are separated. The aqueous layer is extracted again with methylene chloride. The methylene chloride layers are combined and evaporated to a small volume and cooled. The resulting solids are recrystallized from acetone to yield 2,7-bis(5-chloroacetyl)phenoxathiin and 2,8-bis(5-chloroacetyl)phenoxathiin as a mixture. M.P. 199°–206°C.

EXAMPLE 19

2,7-Bis(2-diethylaminoacetyl)phenoxathiin dihydrochloride

A mixture of 24.7 g (0.07 mole) 2,7- and 2,8-bis(2-chloroacetyl)phenoxathiin (mixture from Example 18), 2 g of potassium iodide, 200 ml of diethylamine and 500 ml of tetrahydrofuran is allowed to stand for 7 days and then filtered and the filtrate concentrated. The residual concentrate is dissolved in 10% HCl, filtered, the filtrate is made alkaline and extracted twice with methylene chloride. The extracts are combined, filtered and the filtrate evaporated about one-half volume. After cooling the filtrate is acidified with ethereal HCl to Congo Red. The resulting precipitate is diluted twice with ethyl ether, the solid filtered off and dried. The solid is recrystallized from methanol and diethyl ether and dried to give 2,7-bis(2-diethylaminoacetyl)-phenoxathiin dihydrochloride. M.P. 176°–179°C. The 2,8-isomer was not isolated.

EXAMPLE 20

2,7-Bis(3-diethylaminopropionyl)phenoxathiin dihydrochloride

A mixture of 22.4 g (0.03 mole) 2,7-bis(3-chloropropionyl)phenoxathiin, 1 g of potassium iodide, 75 ml of diethylamine and 75 ml of tetrahydrofuran is allowed to stand for 3 days then filtered and the filtrate evaporated to dryness. The residue is dissolved in ethanol and acidified with etheral HCl to Congo Red. The solution is diluted with ethyl ether and the solid filtered off. The solid is thrice dissolved in methanol, filtered, precipitated with ethyl ether and filtered. The resulting product is dried to give 2,7-bis(3-diethylaminopropionyl)-phenoxathiin dihydrochloride. M.P. 189°–190°C.

The synthesis of additional bis-ω-haloalkanoyl-phenoxathiin starting materials for the preparation of bis-basic ketone derivatives of phenoxathiin are set forth in Netherlands patent 72/09010 which is equivalent to pending U.S. application Ser. No. 158,122, and of which the appropriate examples are incorporated herein by reference thereto. These appropriate bis-ω-haloalkanoylphenoxathiin derivatives may be used with an appropriate amine to prepare addition examples of bis-basic ketone derivatives of phenoxathiin of general Formula I.

EXAMPLE 21

2,8-Bis(4-dimethylaminobutyryl)dibenzothiophene dihydrochloride

A mixture of 28.0 g (0.072 mole) of 2,8-bis(4-chlorobutyryl)dibenzothiophene, 200 ml of 25% aqueous solution of dimethylamine and 2.0 g of potassium iodide in 200 ml of tetrahydrofuran is heated at 125°C with stirring for 24 hours in a Paar general purpose bomb. The reaction mixture is cooled, then filtered, and the filtrate is evaporated in vacuo leaving a residue which is dissolved in ether, treated with ethereal HCl and recrystallized from methanol-acetone to give 2,8-bis(4-dimethylaminobutyryl)dibenzothiophene dihydrochloride. M.P. 93°–95°C.

EXAMPLE 22

$\alpha,\alpha'$-Bis(3-dimethylaminopropyl)dibenzothiophene-2,8-dimethanol

To a cooled, stirred solution of 21.7g (0.053 mole) of 2,8-bis(4-dimethylaminobutyryl)dibenzothiophene dissolved in 200 ml of tetrahydrofuran is added a solution of 4.2 g (0.11 moles) of sodium borohydride contained in a solution of 50 ml of methanol and 5 ml of a 10% sodium hydroxide solution. The resulting mixture is allowed to warm gradually to room temperature and stirring continued overnight. The reaction mixture is diluted with water, and the solid which forms is filtered, washed with water and air dried. The solid product is dissolved in 10% hydrochloric acid solution filtered and the filtrate made alkaline with 10% sodium hydroxide solution. The alkaline filtrate is extracted with methylene chloride. The organic extract is washed with water, followed by a wash of saturated sodium chloride solution, dried over anhydrous magnesium sulfate filtered and evaporated to dryness in vacuo. The residue containing $\alpha,\alpha'$-bis(3-dimethylaminopropyl)dibenzothiophene-2,8-dimethanol is recrystallized twice from benzene.

EXAMPLE 23

Following the procedure of Example 22, only substituting for 2,8-bis(4-dimethylaminobutyryl)dibenzothiophene, appropriate amounts of 2,8-bis(4-diethylaminobutyryl)thioxanthene or 2,7-bis(3-diethylaminopropionyl)phenoxathiin the following respective products are obtained: $\alpha,\alpha'$-bis(3-dimethylaminopropyl)thioxanthene-2,8-dimethanol, $\alpha,\alpha'$-bis(2-diethylaminoethyl)phenoxathiin-2,7-dimethanol.

EXAMPLE 24

2,8-Bis(4-dimethylamino-1-butenyl)dibenzothiophene

A mixture of 10.2 g (0.035 mole) of $\alpha,\alpha'$-bis(3-dimethylaminopropyl)dibenzothiophene-2,8-dimethanol, 25 ml of ethylene glycol monoethyl ether and 25 ml of concentrated hydrochloric acid is heated on a steam bath for 5 minutes. The mixture is then diluted with an equal volume of water and made alkaline with a 20% sodium hydroxide solution and extracted with ether. The ether extracts are combined, washed with water and saturated sodium chloride solution, dried over anhydrous magnesium sulfate, filtered and evaporated to dryness in vacuo. The residue is recrystallized from ethanol and isopropyl alcohol to give 2,8-bis(4-dimethylamino-1-butenyl)dibenzothiophene.

EXAMPLE 25

Following the procedure of example 24, only substituting for $\alpha,\alpha'$-bis(3-dimethylaminopropyl)dibenzothiophene-2,8-dimethanol, appropriate amounts of $\alpha,\alpha'$-bis(3-dimethylaminopropionyl)thioxanthene-2,8-dimethanol or $\alpha,\alpha'$-bis(3-diethylaminoethyl)phenoxathiin-2,7-dimethanol, the follwoing respective products are obtained:
2,8-bis(4-dimethylamino-1-butenyl)thioxanthene,
2,7-bis(3-diethylamino-1-propenyl)phenoxathiin.

17

The following Examples 26–29 are illustrative of suitable pharmaceutical preparations containing compounds of general Formula I.

EXAMPLE 26

An illustrative composition for tablets is as follows:

|     |                                                                      | Per Tablet |
| --- | -------------------------------------------------------------------- | ---------- |
| (a) | 2,8-bis(dimethylaminoacetyl)-dibenzothiophene dihydrochloride        | 100.0 mg   |
| (b) | wheat starch                                                         | 15.0 mg    |
| (c) | lactose                                                              | 33.5 mg    |
| (d) | magnesium stearate                                                   | 1.5 mg     |

A portion of the wheat starch is used to make a granulated starch paste which together with the remainder of the wheat starch and the lactose is granulated, screened and mixed with the active ingredient, that is, (a), and the magnesium stearate. The mixture is compressed into tablets weighing 150 mg each.

EXAMPLE 27

An illustrative composition for a parenteral injection is the following wherein the quantities are on a weight to volume bases.

|     |                                                               | Amount   |
| --- | ------------------------------------------------------------- | -------- |
| (a) | 2,8-bis(4-diethylaminobutyryl)-thioxanthene dihydrochloride   | 100.0 mg |
| (b) | sodium chloride                                               | q.s.     |
| (c) | water for injection to make                                   | 10.0 ml  |

The composition is prepared by dissolving the active ingredient, that is (a), and sufficient sodium chloride in water for injection to render the solution isotonic. The composition may be dispensed in a single ampule containing 100 mg of the active ingredient for multiple dosage or in 10 ampules for single dosage.

EXAMPLE 28

An illustrative composition for hard gelatin capsules is as follows:

|     |                                                                            | Per Capsule |
| --- | -------------------------------------------------------------------------- | ----------- |
| (a) | bis(3-diethylaminopropyl)dibenzothiophene-2,8-dicarboxylate dihydrochloride | 200.0 mg    |
| (b) | talc                                                                       | 35.0 mg     |

The composition is prepared by passing the dry powders of (a) and (b) through a fine mesh screen and mixing them well. The powder is then filled into No. 0 hard gelatin capsules at a net fill of 235 mg per capsule.

EXAMPLE 29

An illustrative composition for pills is as follows:

|     |                                                               | Per Pill |
| --- | ------------------------------------------------------------- | -------- |
| (a) | 2,8-bis(2-dimethylaminoethoxy)-dibenzothiophene dihydrochloride | 200 mg   |
| (b) | corn starch                                                   | 130 mg   |
| (c) | liquid glucose                                                | 20 ml    |

The pills are prepared by blending the active ingredient (a) and the corn starch then adding the liquid glucose with thorough kneading to form a plastic mass from which the pills are cut and formed.

EXAMPLE 30

2,7-Bis(5-diallylaminovaleryl)thioxanthene

A mixture of 22.3 g (0.05 mole) of 2,7-bis(5-chlorovaleryl)thioxanthene, 1 g of potassium iodide, 100 ml of diallylamine and 200 ml of tetrahydrofuran is placed in a Paar bomb and heated to 120°C with stirring for 24 hours. Upon cooling, the mixture is filtered and the filtrate evaporated to dryness. The resulting residue is dissolved in dilute HCl and extracted with ether. The aqueous portion is made basic, extracted with methylene chloride, dried over magnesium sulfate and filtered. The filtrate is heated to boiling, treated with charcoal, filtered and filtrate evaporated to dryness. The residue is chromatographed on a column of alumina and eluted with methylene chloride. The resulting oil is dissolved in diethyl ether, dried over molecular sieves, filtered and the ether evaporated. This process is repeated several times to yield 2,7-bis(5-diallylaminovaleryl)thioxanthene.

I claim:

1. A method of treating conditions of delayed hypersensitivity which comprises administering to a patient in need thereof a compound selected from the formula

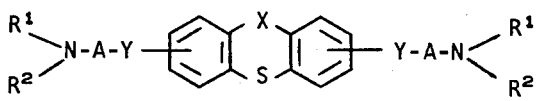

wherein X is selected from a bond, —CH$_2$—, or oxygen; each Y is selected from a vinylene group,

carbonyl, oxygen, divalent sulfur, or carbonyloxy with the proviso that when Y is selected from oxygen, divalent sulfur or carbonyloxy, X is a bond; A is selected from a straight or branched alkylene chain of from 1 to 6 carbon atoms with the proviso that when Y is a vinylene group, A contains from 1 to 5 carbon atoms and with the proviso that when Y is carbonyloxy, A contains from 2 to 6 carbon atoms; each R$^1$ and R$^2$ is selected from hydrogen, a straight or branched alkyl group of from 1 to 4 carbon atoms, or alkenyl of 3 to 6 carbon atoms having the vinyl unsaturation in other than the 1-position; and pharmaceutically acceptable acid addition salts thereof, in an amount effective to suppress delayed hypersensitivity.

2. A method of claim 1 wherein each of R$^1$ and R$^2$ is straight or branched lower alkyl of from 1 to 4 carbon atoms.

3. A method of claim 2 wherein each Y is a vinylene group.

4. A method of claim 2 wherein each Y is

5. A method of claim 2 wherein each Y is carbonyl.
6. A method of claim 2 wherein each Y is oxygen.
7. A method of claim 2 wherein each Y is divalent sulfur.
8. A method of claim 2 wherein each Y is carbonyloxy.
9. A method of claim 5 wherein the compound is 2,8-bis(2-diethylaminoacetyl)thioxanthene or a pharmaceutically acceptable acid addition salt thereof.

* * * * *

UNITED STATES PATENT AND TRADEMARK OFFICE
CERTIFICATE OF CORRECTION

PATENT NO. : 3,937,835
DATED : February 10, 1976
INVENTOR(S) : Irving Shemano

It is certified that error appears in the above-identified patent and that said Letters Patent are hereby corrected as shown below:

Column 8, line 6 "...diamines by aa Sandmeyer..." should read "...diamines by a Sandmeyer...". Column 12, line 10 "...consisting of C. 40%..." should read "...consisting of approximately 40%...". Column 16, line 63 "...α,α'-bis-(3-dimethylaminopropionyl)thio..." should read "...α,α'-bis-(3-dimethylaminopropyl;thio...".

Signed and Sealed this

Twenty-second Day of February 1977

[SEAL]

*Attest:*

RUTH C. MASON
*Attesting Officer*

C. MARSHALL DANN
*Commissioner of Patents and Trademarks*